United States Patent [19]
Baranitsky

[11] Patent Number: 5,954,679
[45] Date of Patent: Sep. 21, 1999

[54] ADHESIVE BANDAGE

[76] Inventor: Dean Baranitsky, Box 2101, Whitecourt, Alberta, Canada, T7S 1P1

[21] Appl. No.: 09/136,691

[22] Filed: Aug. 19, 1998

[51] Int. Cl.$^6$ .......................................... A61F 5/00
[52] U.S. Cl. .................. 602/41; 602/57; 602/58; 128/888; 128/889
[58] Field of Search ............... 602/41–59; 604/304, 604/307, 358, 346, 369, 372, 386; 128/888, 889, 890; D24/189

[56] References Cited

U.S. PATENT DOCUMENTS

| | | |
|---|---|---|
| 2,992,644 | 7/1961 | Plantinga . |
| 3,927,669 | 12/1975 | Glatt . |
| 4,285,338 | 8/1981 | Lemelson . |
| 4,561,435 | 12/1985 | McKnight et al. ............ 602/59 X |
| 4,616,644 | 10/1986 | Saferstein . |
| 5,170,781 | 12/1992 | Loomis . |
| 5,336,209 | 8/1994 | Porzilli ............................ 604/307 |

*Primary Examiner*—Richard J. Apley
*Assistant Examiner*—Kim M. Lee
*Attorney, Agent, or Firm*—Davis and Bujold

[57] ABSTRACT

An adhesive bandage includes a flexible planar abrasion resistant body having an outer face, an inner face, and a peripheral edge. A sterile pad is secured to the inner face of the abrasion resistant body. A covering of flexible material is secured to the outer face of the abrasion resistant body and extends past the abrasion resistant body to form wings. The wings have an adhesive coating whereby the wings may be adhered to human skin to maintain the sterile pad in position over a wound. The covering is attached to the abrasion resistant body immediately adjacent to the peripheral edge leaving an unsecured central portion of the covering extending across the second face of the abrasion resistant body. Rubbing results in movement of the unsecured central portion of the covering against the abrasion resistant body thereby insulating the sterile pad from movement due to said rubbing.

3 Claims, 2 Drawing Sheets

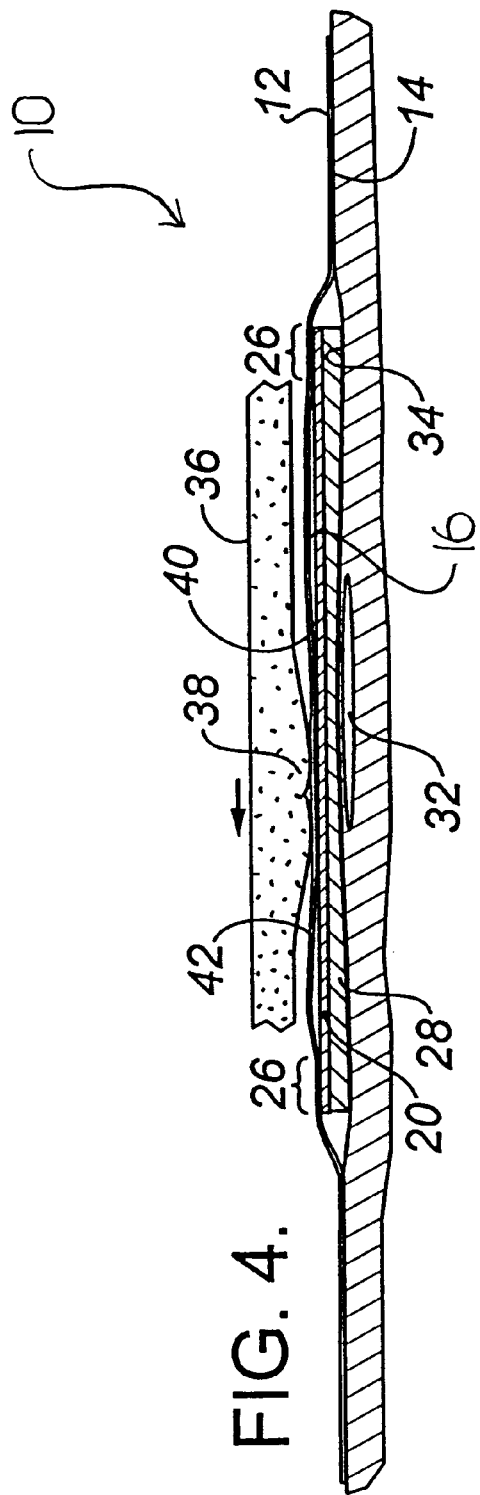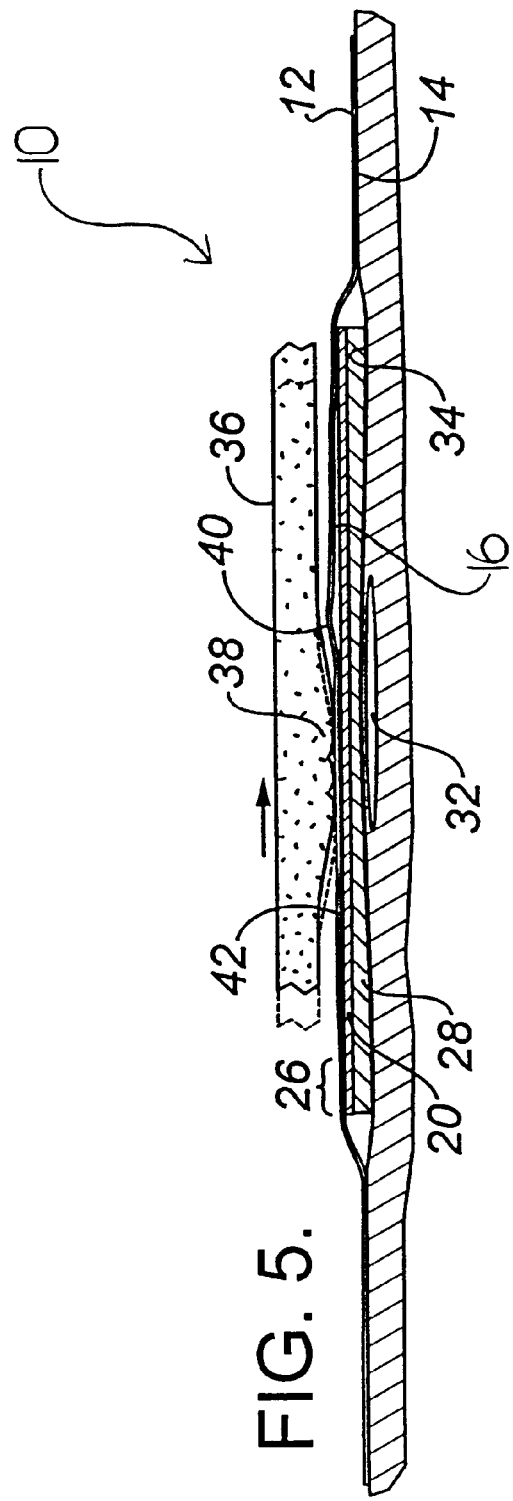

ADHESIVE BANDAGE

FIELD OF THE INVENTION

The present invention relates to an adhesive strip-form bandage used to cover minor cuts and blisters.

BACKGROUND OF THE INVENTION

Adhesive bandages consist of a sterilized pad centrally mounted on a relatively larger adhesive strip, such that a portion of the adhesive strip protrudes past the sterilized pad on two or more sides to form wings. When the sterilized pad is placed over a minor injury, such as a cut, the protruding wings of the adhesive strip adheres to the skin to maintain the sterile pad in position.

Adhesive bandages are often not effective in providing protection to blisters. This is particularly the case with blisters received when a person walks in ill-fitting footwear and a portion of the footwear repeatedly rubs against the person's skin. When a person receives a cut, the person's skin is subjected to a one time trauma. With a blister the person's skin is subjected to a repeat of the initial trauma everytime the ill-fitting footwear is worn. The best solution is, of course, to avoid wearing the ill-fitting footwear. This is not always a practical solution.

SUMMARY OF THE INVENTION

What is required is an adhesive bandage that provides more effective protection against rubbing.

According to the present invention there is provided an adhesive bandage which includes a flexible planar abrasion resistant body having an outer face, an inner face, and a peripheral edge. A sterile pad is secured to the inner face of the abrasion resistant body. A covering of flexible material is secured to the outer face of the abrasion resistant body and extends past the abrasion resistant body to form wings. The wings have an adhesive coating whereby the wings may be adhered to human skin to maintain the sterile pad in position over a wound. The covering is attached to the abrasion resistant body immediately adjacent to the peripheral edge leaving an unsecured central portion of the covering extending across the second face of the abrasion resistant body. Rubbing results in movement of the unsecured central portion of the covering against the abrasion resistant body thereby insulating the sterile pad from movement due to said rubbing.

With the adhesive bandage, as described above, the abrasion resistant body serves to protect the blister from being aggravated by rubbing. The rubbing is dissipated by movement of the flexible outer covering against the abrasion resistant body. This prevents the sterile pad from moving on the wound. Polymer plastic has been found to be suitable for use as abrasion resistant shielding material.

Although beneficial results may be obtained through the use of the invention, as described above, air is viewed as playing a valuable role in the healing process. Even more beneficial results may, therefore, be obtained when the abrasion resistant body has a plurality of aeration perforations.

BRIEF DESCRIPTION OF THE DRAWINGS

These and other features of the invention will become more apparent from the following description in which reference is made to the appended drawings, wherein:

FIG. 4 is a second side elevation view, in section, of the adhesive bandage illustrated in FIG. 1, placed over a blister.

FIG. 5 is a third side elevation view, in section, of the adhesive bandage illustrated in FIG. 1, placed over a blister.

DETAILED DESCRIPTION OF THE PREFERRED EMBODIMENT

Figure 1:
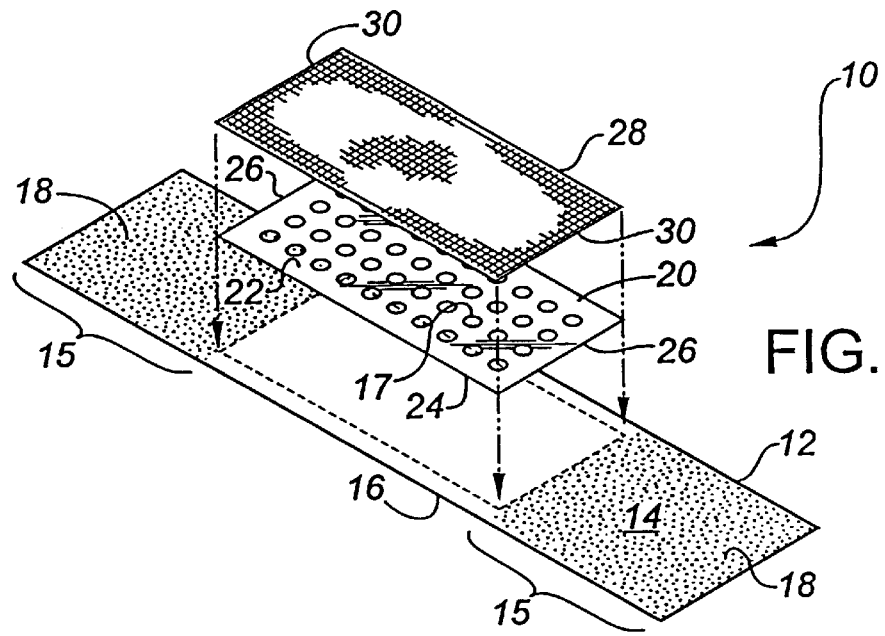
FIG. 1 is an exploded perspective view of an adhesive bandage made in accordance with the teachings of the present invention.
Figure 2:
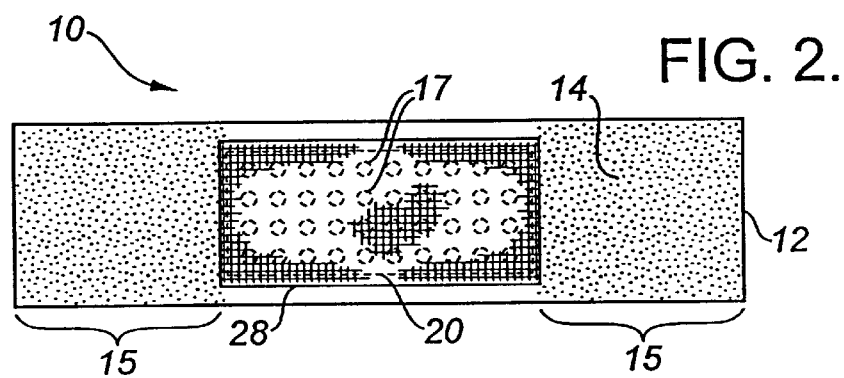
FIG. 2 is a top plan view of the adhesive bandage illustrated in FIG. 1.

The preferred embodiment, an adhesive bandage generally identified by reference numeral 10, will now be described with reference to FIGS. 1 through 5.

Figure 3:
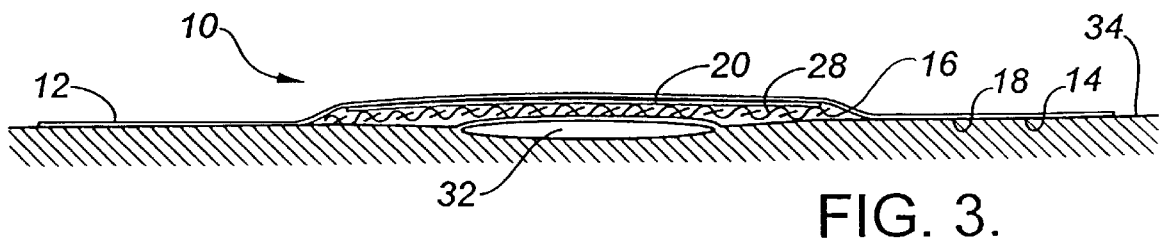
FIG. 3 is a first side elevation view, in section, of the adhesive bandage illustrated in FIG. 1, placed over a blister.

Referring to FIG. 1, adhesive bandage 10 includes a flexible planar abrasion resistant body 20 having an inner face 22, an outer face 24, and a peripheral edge 26. Polymer plastic has proven to be an effective abrasion resistant shield. A sterile pad 28 is secured to inner face 22 of abrasion resistant body 20. Sterile pad 28 has a peripheral edge 30 that is coterminous with peripheral edge 26. A covering 12 of flexible material is secured to outer face 24 of abrasion resistant body 20. Covering 12 extends past abrasion resistant body 20 to form wings 15. Wings 15 have an adhesive coating 14 whereby wings may be adhered to human skin 34, as illustrated in FIGS. 3 through 5, to maintain sterile pad 28 in position over a wound such as blister 32. Referring to FIG. 1, covering 12 is attached to abrasion resistant body 20 immediately adjacent to peripheral edge 26 leaving an unsecured central portion 16 of covering 12 extending across second face 24 of abrasion resistant body 20. It is preferred that abrasion resistant body have a plurality of aeration perforations 17.

The use of adhesive bandage 10 will now be described with reference to FIGS. 1 through 5. Referring to FIG. 3, sterile pad 28 of adhesive bandage 10 is positioned over blister 32. Sterile pad 28 is then maintained in position by adhering adhesive 14 on wings 15 of covering 12 to unaffected human skin 34 adjacent blister 32. FIGS. 4 and 5 illustrate what occurs when an abrasive portion 38 of ones footwear 36 rubs against adhesive bandage 10 first in one direction and then in the opposite direction. With other types of adhesive bandages, the layers are bonded together. This results in the sterile pad moving across the wound. With adhesive bandage 10 rubbing results in movement of unsecured central portion 16 of covering 12 against abrasion resistant body 20. It is to be noted that covering 12 is secured along peripheral edge 26. That portion of covering 12 does not move. Movement does occur in unsecured central portion 16 of covering 12. Referring to FIGS. 4 and 5, unsecured central portion 16 can be considered to be divided into two portions 40 and 42 at the point of contact of abrasive portion 38 of footwear 36. Referring to FIG. 4, when the rubbing force is one direction, as indicated by the arrow, portion 40 is placed in tension and pulled taut while portion 42 is placed in compression with material being pushed ahead of abrasive portion 38 toward peripheral edge 26. Referring to FIG. 5, when the rubbing force is in the other direction, as indicated by the arrow, portion 42 is placed in tension and pulled taut while portion 40 is placed in compression with material being pushed ahead of abrasive portion 38. It can be seen how the rubbing is dissipated by movement of the flexible outer covering 12 against abrasion resistant body 20. This prevents sterile pad 28 from moving on blister 32.

It will be apparent to one skilled in the art that modifications may be made to the illustrated embodiment without departing from the spirit and scope of the invention as hereinafter defined in the claims.

The embodiments of the invention in which an exclusive property of privilege is claimed are defined as follows:

1. An adhesive bandage, comprising:

a flexible planar abrasion resistant body having an outer face, an inner face, and a peripheral edge;

a sterile pad secured to the inner face of the abrasion resistant body;

a covering of flexible material secured to the outer face of the abrasion resistant body and extending past the abrasion resistant body to form wings, the wings having an adhesive coating wherein the wings may be adhered to human skin to maintain the sterile pad in position over a wound, the covering being attached to the abrasion resistant body immediately adjacent to the peripheral edge leaving an unsecured central portion of the covering extending across the second face of the abrasion resistant body such that rubbing results in movement of the unsecured central portion of the covering against the abrasion resistant shield thereby insulating the sterile pad from movement due to said rubbing.

2. The adhesive bandage as defined in claim 1, wherein the abrasion resistant covering is of polymer plastic.

3. The adhesive bandage as defined in claim 1, wherein the abrasion resistant covering has a plurality of aeration perforations.

* * * * *